(12) United States Patent
Carthron

(10) Patent No.: US 6,277,842 B1
(45) Date of Patent: Aug. 21, 2001

(54) DIETARY SUPPLEMENTAL METHOD FOR FAT AND WEIGHT REDUCTION

(76) Inventor: James Alexander Carthron, 4901 McWillie Cir., Apt. -801, Jackson, MS (US) 39206

( * ) Notice: Subject to any disclaimer, the term of this patent is extended or adjusted under 35 U.S.C. 154(b) by 0 days.

(21) Appl. No.: 09/690,880

(22) Filed: Oct. 17, 2000

(51) Int. Cl.$^7$ .................. A61K 31/555; A61K 31/425; A61K 31/44; A61K 31/35; A61K 31/195
(52) U.S. Cl. .................. 514/188; 514/351; 514/365; 514/451; 514/556; 514/565
(58) Field of Search .................. 514/188, 351, 514/365, 451, 556, 565

(56) References Cited

U.S. PATENT DOCUMENTS

| | | | |
|---|---|---|---|
| 5,164,384 | * 11/1992 | Paul | 514/188 |
| 5,340,315 | * 8/1994 | Kaye | 434/127 |
| 5,480,657 | 1/1996 | Allen . | |
| 5,626,849 | 5/1997 | Hastings . | |
| 5,716,926 | 2/1998 | Beale . | |
| 5,730,988 | 3/1998 | Womack . | |
| 5,817,329 | 10/1998 | Gardiner . | |
| 5,889,040 | 3/1999 | Beale . | |
| 5,905,075 | 5/1999 | Harpe . | |
| 5,911,992 | 6/1999 | Braswell . | |
| 5,914,326 | 6/1999 | McCarty . | |
| 5,925,377 | 7/1999 | Gerth . | |
| 5,948,772 | 9/1999 | de la Harpe . | |
| 5,962,030 | 10/1999 | Fine . | |
| 5,976,550 | 11/1999 | Engel . | |
| 5,980,905 | 11/1999 | Harpe . | |
| 6,008,252 | 12/1999 | Beale . | |

OTHER PUBLICATIONS

Boyle, et al., Chromium Depletion in the Pathogenesis of Diabetes and Atherosclerosis, Southern Medical Journal, 1977, vol. 70(12), pp. 1449–1453.

Anderson and Kozlovsky, Chromium intake, absorption and excretion of subjects consuming self–selcted diets, The American Journal of Clinical Nutrition, vol.–41, pp. 1177–1183, 1985.

Kaats, et al., Effects of Chromium Picolinate Supplementation on Body Composition: a Randomized, Curr. Thera. Res. vol. 57 (10), pp. 747–756, 1996.

Stanko, et al., Pyruvate Supplementation of a low–cholesterol, low–fat diet: effects on plasma lipid, Am. J. Clinical Nutrition, vol. 59, pp. 423–427, 1994.

Bruno, Gene, The Top Ten Fat Burners, Total Health, vol. 20 (4), 1998 (Aug./Sep), Total Health Communications pp. 22–24.

Sinatra, Stephen, Wonders of CoQ10, Total Health, vol. 19 (3), p22, 1997 (Jul./Aug.) , Total Health Communications.

Conley, Edward, When holiday Fatigue Doesn't Go Away, Better Nutrition, vol.61 (11) p. 32, 1999 (Nov), Sabot Publishing.

Scheer and Anderson–Parrado, B Vitamins, Better Nutrition, vol. 61 (4) p. 54–57, 1999 (Apr.), Sabot Publishing.

Mani, Josephine, Nutrients first pyruvate the natural path to weight loss, Total Health, vol. 20(1), pp. 36–38 1998, (Feb./Mar.), Total Health Communications.

Morgan, Peggy, Consumer's Guide to Supplements, Prevention, vol. 50 (4), pp. 112–121, 1998 (Apr.), Rodale Press Inc.

Challem, Jack Who need the "Super" Supplements? Vegetarian Times, Issue 247, pp. 58–61, 1998 (Mar.), Sabot Publishing.

* cited by examiner

*Primary Examiner*—Raymond Henley, Jr.

(57) ABSTRACT

A natural method for promoting fat, and weight loss while decreasing food cravings comprising administrating to an individual in need thereof L-carnitine, chromium, coenzyme Q10, creatine, lipoic acid, niacin, pyruvate, riboflavin, and thiamine. Pyruvate is a major promoter of the oxidation of dietary fuels like carbohydrates and fatty acids in the citric acid cycle. L-carnitine allow the transport of fatty acids into the mitochondria were they can be degraded in the citric acid cycle. Lipoic acid is a major intracellular antioxidant, and component of key enzymes in the citric acid cycle. Niacin, riboflavin, and thiamine are key components of enzymes that lead to the breakdown of dietary fuel molecules such as fatty acids, amino acids, and carbohydrates that enter the citric acid cycle. The breakdown of these dietary fuels leads to the production of high energy hydrogen atoms. Coenzyme Q10 accepts these hydrogen atoms and utilizes them for cellular energy production. Chromium helps reduce food cravings by normalizing insulin levels. Creatine allows increased storage of cellular energy, and promotes lean muscle tissue.

10 Claims, No Drawings

DIETARY SUPPLEMENTAL METHOD FOR FAT AND WEIGHT REDUCTION

BACKGROUND—FIELD OF INVENTION

The present invention relates to a method for promoting fat, and weight loss. This method also helps increase lean muscle mass in the individual user. More particularly, the invention relates to coadministration of L-carnitine, chromium, creatine, lipoic acid, niacin, pyruvate, riboflavin, thiamine, and Coenzyme Q10.

BACKGROUND—DISCUSSION OF PRIOR ART

Many current weight-lose strategies require significant limitations on the amount of caloric intake, and the amount of fat, and carbohydrates consumed by an individual. However, due to the inherent causes of obesity, and overeating, dieting by itself is often unsuccessful in achieving individual goals. There are two primary reasons for this. First, there is an immense amount of patience required by the dieter to lose significant amounts of weight. Second, and perhaps more important, are the inherent reasons that the vast majority of over-eating is done to satisfy anxiety. This fact lead to the development of another type of weight control method known collectively as the appetite suppression.

In the past, appetite suppression has been accomplished by the use of centrally-acting neuro-stimulants such as cocaine, caffeine, methamphetamine hydrochloride, dextroamphetamine sulfate, and other derivatives of the amphetamine molecule. These drugs typically are effective for a short period of time, but tachyphylaxis invariably develops, and there are other inherent side-effects, such as nervousness, insomnia, and GI tract irritation, which develop with the use of such drugs.

Other methods such as aerobic exercise and, weight training have also been tried without a great deal of success. These techniques usually require some level of skill and a high degree of motivation among users. There has also been considerable interest in high protein, low carbohydrate, diets. Such diets have been hypothesized to promote ketosis, which in turn decreases appetite while sparing body protein. However, it is as yet uncertain whether these diets are more successful than others in reducing body weight, and there have been a relatively large number of unexplained sudden deaths in patients on these diets.

Chitosan has recently been proposed as weight reduction product because of its ability to attract part of the fat consumed during a meal. Chitosan must however, be eaten within a half-hour before a meal. Chitosan acts electrostatically to attract part of the fat that is consumed during a meal and carries it through the body undigested. This can lead to a osmotic diarrhea because of the excessive solute load.

However effective chitosan may be at removing fat, it does not function as a deterrent to the amount of food or fat which one may ingest during a meal. Chitosan has no effect on carbohydrate metabolism, and subsequent conversion to fat. Furthermore, chitosan does not have any effect on fat already stored by the body.

Certain Amino acids and their derivatives have also been proposed in many popular weight lose schemes. However, in the absence of starvation, or reduced blood glucose levels, amino acids are preferentially used as building blocks in biosynthetic reactions. The most important of these reactions being the synthesis of tissue proteins. Amino acids are used secondarily as a fuel and a typical western diet provides only about one fifth of the daily energy requirement.

There is a need in the art for an weight control method that is convenient for the user. The method should actively promotes fat, and weight reduction without significant side-effects. There is also a need to naturally reduce the users urge to over-eat. This invention fulfills these needs, and provides other related advantages.

OBJECTS AND ADVANTAGES

Accordingly, besides the objects and advantages of a convenient, and effective method for reducing fat, and weight described in my above patent, several objects, and advantages are:

a.) This invention offers a fast, and effective fat, and weight reduction method. It has proven efficacy, and a low side effect profile of all components in the above invention.

b.) The above invention can be taken before, during, or after meals with no decrease in effectiveness.

c.) The above invention does not induce tachyphylaxsis, GI tract irritation, insomnia, or psychomotor agitation.

d.) The above invention provides removal of both dietary, and stored fat without the need for conscious efforts to diet by the user.

e.) The above invention does not cause diarrhea.

f) For those who do find it appropriate to diet, L-carnitine accelerates the loss of body fat without sacrificing excessive loss of lean mass.

g.) Studies of athletes supplementing their diet with L-carnitine showed a significant increase in the use of fat during exercise.

h.) Chromium is an insulin co-factor that naturally helps control appetite, and food craving by normalizing insulin levels.

i.) Chromium also plays a part in the growth of muscle, and the control of body fat.

j.) Lipoic acid increases glucose uptake by muscle cells, and decreases glucose uptake by fat cells. As part of the glycolytic pathway, lipoic acid both stimulates insulin activity, and reduces insulin resistance. This helps move glucose out of the blood, and into-the cells so more gets utilized.

k.) Lipoic acid increases the efficiency with which glucose is used within cells. It has been shown to enhance the burning of glucose in obese laboratory animals in a way that is comparable to, but independent of, insulin.

l.) According to Dr. Hans Tritschler, a researcher from Munich Germany, lipoic acid can increase the conversion, and storage of glucose as ATP by approximately 40%. It does this through a variety of mechanisms including the stimulation of GLUT-1 and GLUT-4 glucose transporters.

m.) Studies conclude that increasing muscular creatine may also increase muscle proteins, as well as reduce muscle protein breakdown. This indicates that creatine supplementation may have an impact on muscle growth and recuperation by preserving muscle fibers.

n.) Creatine also buffers lactic acid build-up allowing for a more enduring exercise routine. Lactic acid is the main cause of exercise-related muscle fatigue.

o.) Pyruvate has been shown, in studies carried out on laboratory animals, to have a appetite decreasing effect.

Other objects and advantages of the above invention are:

p.) L-carnitine also reduces fatigue, is used in the treatment of atherosclerotic heart diseased, advantageously increases HDL cholesterol while lowering LDL cholesterol, and decreased ketone levels in the blood.

q.) Chromium also plays an important role in controlling blood lipids, lowering harmful LDL cholesterol and increasing beneficial HDL cholesterol.

r.) Lipoic acid is a powerful antioxidant. Most antioxidants like vitamin C and E are too large to pass through the cell membrane and thus offer protection only on the outside of the cell. Lipoic acid is a very small molecule which can easily pass through the cell membrane providing free radical protection both inside and outside of the cell.

s.) Lipoic acid has been shown to alleviate the symptoms of neuropathy in diabetics by reducing oxidized sugar molecules trapped in nerve fibers.

t.) Lipoic acid directly recycles vitamin C and indirectly recycles vitamin E, it also stimulates the production of glutathione, the most important antioxidant made by the body.

u.) Lipoic acid helps protect muscle from free radical damage improving recovery and reducing soreness after strenuous activity.

v.) Because lipoic acid is a sulfur compound it can bind and help eliminate heavy metals such as copper, iron, and, mercury, risk factors for a wide range of degenerative diseases.

w.) Supplemental lipoic acid also maintains a normal ratio of reduced-to-oxidized coenzyme Q10 x.) CoQ10 has been proven to be effective for healing specific muscle disorders, particularly those relating to the heart.

y.) By boosting the energy output of heart cells, CoQ10 makes heart muscles stronger and better able to pump blood.

z.) Coenzyme Q10 is also used to maintain immune function, lower blood pressure and as a powerful antioxidant.

Further objects and advantages of my invention will become apparent from a consideration of the ensuing description.

SUMMARY OF THE INVENTION

One embodiment of the present invention is a method of promoting weight and fat loss in an individual in need thereof, comprising coadministration to the individual daily effective weight and fat loss-promoting amounts of L-carnitine, chromium, creatine, lipoic acid, niacin, pyruvate, riboflavin, thiamine, and coenzyme Q10 (CoQ10). Preferably the effective amount of L-carnitine is between about 50 mg and 20 grams. This invention may further comprise administration an effective daily weight, and fat loss promoting amount of chromium as chromium picolinate. Preferably, the effective amount is between about 30 mcg and 2500 mcg.

The invention may further comprise administration an effective daily weight and fat loss promoting amount of lipoic acid as alpha-lipoic acid. The preferable effective amount is between about 30 mg and 6000 mg. Preferably, the effective amount of creatine is between about 25 mg and 50 grams. Preferably, the effective amount of coenzyme Q10 is between about 10 mg and 2400 mg.

This invention preferably uses niacin in either the form nicotinic acid or nicotinamide. Preferably, the effective amount is between about 6 mg and 120 mg. Preferably, the effective amount of pyruvate is between about 30 mg and 60 grams. Preferably, the effective amount of riboflavin is between about 1.2 mg and 250 mg. Preferably, the effective amount of thiamine is between about 1 mg and 1000 mg.

DETAILED DESCRIPTION

Without wishing to be bound by any particular theory, it is believed that this invention will function by several complementary mechanisms related to the citric acid cycle (TCA cycle) and insulin metabolism.

Pyruvate enhances both fat and weight loss by two mechanisms. Pyruvate increases resting metabolic rate. Pyruvate also increases the metabolism of fats and carbohydrates. The major function of carbohydrates and fatty acids is to provide energy through their oxidation in the citric acid cycle. Increased pyruvate levels serve to prime the citric acid cycle and allows the increased utilization of carbohydrates, and fatty acids in the TCA cycle.

Lipoic acid is a cofactor in two multi-enzyme complexes pyruvate dehydrogenase (PDH) and alpha-ketoglutarate dehydrogenase. These enzymes are part of the citric acid cycle (actually, PDH connects glycolysis with the TCA cycle) and are thus essential in the conversion of food into energy.

Niacin, and riboflavin, in their cofactor forms promote continued activation of the citric acid cycle by reversibly accepting high energy hydrogen atoms produced in the TCA cycle. Niacin, and riboflavin also accept hydrogen atoms produced during the degradation of fatty acids, and pyruvate.

Without niacin, and riboflavin these hydrogen atoms would tend to build up and slow the reactions of the citric acid cycle by the process of product inhibition. Thiamine, in a cofactor form that require the high energy groups of adenosine triphosphate, serves as a cofactor in the oxidative decarboxylation of alpha-keto acids used in the TCA cycle.

The primary role of L-carnitine in the body is as a biocatalyst. Fats are degraded for energy inside muscle cells in the cell organelle known as the mitochondria. Fats are stored in adipose cells and cannot pass through the mitochondria unless they are transported by L-carnitine. Thereupon, the amount of fat degraded in the body depends on the level of L-carnitine in the muscle. The higher the level of L-carnitine in the body, the greater the amount of body fat used for fuel.

Chromium is an important nutrient for controlling blood sugar. It helps overcome sugar cravings, a problem experienced by many overweight people due to diets high in sugars and refined carbohydrates. Chromium also helps level out the highs and lows of a high carbohydrate diet and, promotes a steady stream of available glucose for continuous, prolonged energy.

Coenzyme Q10 is also called a ubiqinone because it is present in nearly all cells of the body, is obtained from the diet, and is also produced by the body. Like L-carnitine, CoQ10 plays an important role with mitochondria. The electron transport chain, located in the mitochordrial membrane, is the final acceptor of high energy hydrogen atoms produced in TCA cycle.

CoQ10 is an integral component of the electron transport chain. CoQ10 can accept hydrogen atoms produced in the glycolytic pathway, TCA cycle as well as those produced in fatty acid degradation, and the glycerol phosphate shuttle. These hydrogen atoms are ultimately used to produce adenosine triphosphate (ATP), carbon dioxide, and water. ATP is the energy storehouse of the body, and is used for such processes as muscle contraction. Thus, CoQ10 helps prevent product inhibitions, and steers the reactions of the TCA cycle toward dietary fuel degradation.

In skeletal muscle creatine is phosphorlated to phosphorylcreatine. When the muscle is worked, ATP is broken down into ADP (adenosine diphosphate) and energy is released. The high energy phosphates stored in phosphorylcreatine are used to rapidly convert ADP back to ATP. This replaces the ATP consumed during exercise.

The amount of ATP stored in the muscle will only fuel a maximum effort such as lifting a weight for 10 to 15 seconds. After that, the muscle must rely on creatine to restock its ATP supply. Muscle fatigue occurs when the phosphorylcreatine in the muscle is exhausted and the ADP can no longer be converted into the necessary ATP. Thus, supplementing creatine helps to increase the rate in which the body can supply ATP, thereby improving the overall anaerobic efficiency of the muscle.

For oral administration, the components may be provided as a tablet, aqueous or oil suspension, dispersible powder or granule, emulsion, hard or soft capsule, syrup or elixir. Compositions intended for oral use may be prepared according to any method known in the art for the manufacture of pharmaceutically acceptable compositions. Pharmaceutically acceptable means that the agent should be acceptable in the sense of being compatible with the other ingredients of the formulation (as well as non-injurious to the patient).

Such compositions may contain one or more of the following agents: sweeteners, flavoring agents, coloring agents and preservatives. The sweetening and flavoring agents will increase the palatability of the preparation. Tablets containing chromium picolinate in admixture with non-toxic pharmaceutically acceptably excipients suitable for tablet manufacture are acceptable. Such excipients include inert diluents such as calcium carbonate, sodium carbonate, lactose, calcium phosphate or sodium phosphate; granulating and disintegrating agents, such as corn starch or alginic acid; binding agents such as starch, gelatin or acacia; and lubricating agents such as magnesium stearate, stearic acid or talc.

Tablets may be uncoated or may be coated by known techniques to delay disintegration and absorption in the gastrointestinal tract and thereby provide a sustained action over a longer period of time. For example, a time delay material such as glyceryl monostearate or glyceryl distearate alone or with a wax may be employed.

Formulations for oral use may also be presented as hard gelatin capsules wherein the active ingredient is mixed with an inert solid siluent, for example calcium carbonate, calcium phosphate or kaolin, or as soft gelatin capsules wherein the active ingredient is mixed with water or an oil medium, such as peanut oil, liquid paraffin or olive oil. Aqueous suspensions may contain the components in admixture with excipients suitable for the manufacture of aqueous suspensions. Such excipients include suspending agents, dispersing or wetting agents, one or more preservatives, one or more coloring agents, one or more flavoring agents and one or more sweetening agents such as sucrose or saccharin.

Oil suspensions may be formulated by suspending the active ingredient in a vegetable oil, such as arachis oil, olive oil, sesame oil or coconut oil, or in a mineral oil such as liquid paraffin. The oil suspension may contain a thickening agent, such as beeswax, hard paraffin or cetyl alcohol. Sweetening agents, such as those set forth above, and flavoring agents may be added to provide a palatable oral preparation. These compositions may be preserved by an added antioxidant such as ascorbic acid.

Dispersible powders and granules of the invention suitable for preparation of an aqueous suspension by the addition of water provide the active ingredient in admixture with a dispersing of wetting agent, a suspending agent, and one or more preservatives. Additional excipients, for example sweetening, flavoring and coloring agents, may also be present.

Syrups and elixirs may be formulated with sweetening agents, such as glycerol, sorbitol or sucrose, Such formulations may also contain a demulcent, a preservative, a flavoring or a coloring agent.

Adjuvants activity such as aerobic exercise, weight bearing exercise, bathing in warm to moderately hot water to increase body temperature, and heart rate may be used in conjunction with the above invention. These adjuvant activities act synergistically to enhance the activity of the above invention.

Although the above invention has been described in connection with certain specific embodiments, it will be readily apparent to those skilled in the art that various changes can be made to suit specific requirements without departing from the spirit of and scope of the invention.

I claim as my invention:

1. A method for promoting weight and fat loss in an individual in need thereof, comprising coadministration to said individual daily effective weight and fat loss-promoting amounts of L-carnitine, chromium picolinate, creatine, alpha-lipoic acid, niacin, pyruvate, riboflavin, thiamine, and coenzyme Q10.

2. The method of claim 1, wherein said effective amount of L-carnitine is between about 50 mg and 20 grams.

3. The method of claim 1, wherein said effective amount of creatine is 25 mg and 50 gram.

4. The method of claim 1, wherein said effective amount of coenzyme Q10 mg is 10 mg and 600 mg.

5. The method of claim 1, wherein said effective amount of pyruvate is between about 30 mg and 60 grams.

6. The method of claim 1, wherein said effective amount of riboflavin is between about 1.2 mg and 250 mg.

7. The method of claim 1, wherein said effective amount of thiamine is between about 1 mg and 1000 mg.

8. The method of claim 1, wherein said effective amount of chromium picolinate is between about 30 mcg and 2500 mcg.

9. The method of claim 1, wherein said effective amount of alpha-lipoic acid is between about 30 mg and 6.0 grams.

10. The method of claim 1, wherein said effective amount of niacin is between about 6 mg and 120 mg.

* * * * *